United States Patent [19]

Siczek et al.

[11] Patent Number: 5,129,911
[45] Date of Patent: Jul. 14, 1992

[54] ORBITAL AIMING DEVICE

[76] Inventors: Bernard W. Siczek; Aldona A. Siczek, both of 1252 Chinook Way, Boulder, Colo. 80303

[21] Appl. No.: 667,011

[22] Filed: Mar. 11, 1991

[51] Int. Cl.5 ............................................. A61B 19/00
[52] U.S. Cl. .................................... 606/130; 378/162
[58] Field of Search .................. 606/130; 378/37, 99, 378/162

[56] References Cited

U.S. PATENT DOCUMENTS

| 4,230,117 | 10/1980 | Anichkov | 606/130 |
|---|---|---|---|
| 4,386,602 | 6/1983 | Sheldon et al. | 606/130 X |
| 4,583,537 | 4/1986 | Derechinsky et al. | 606/130 |
| 4,722,336 | 2/1988 | Kim et al. | 606/130 |
| 4,750,487 | 6/1988 | Zanetti | 606/130 |
| 4,791,934 | 12/1988 | Brunnett | 606/130 |
| 4,841,967 | 6/1989 | Chang et al. | 606/130 |
| 4,923,459 | 5/1990 | Nambu | 606/130 |
| 4,955,891 | 9/1990 | Carol | 606/130 |

FOREIGN PATENT DOCUMENTS

| 2115121 | 10/1972 | Fed. Rep. of Germany | 606/130 |
|---|---|---|---|
| 2640248 | 3/1978 | Fed. Rep. of Germany | 378/37 |

Primary Examiner—Peter A. Aschenbrenner

[57] ABSTRACT

This invention relates to an orbital aiming device for aiming a puncturing instrument to a targeted object for use with a fluoro X-ray apparatus isocentric in at least one direction.

The orbital aiming device in order to offer most advantages is isocentric about two rotational axes which point of intersection defines its isocenter and is disposed in relation to the fluoro X-ray apparatus so that its isocenter coincides with the isocenter of the X-ray apparatus.

The device comprises an arm for supporting the puncturing instrument so that it aims to the isocenter, which arm is orbitaly moveable on arcuate rails for pivoting the puncturing instrument about the isocenter around one of the two rotational axes the arcuate rails are supported by a supporting means in a rotational relationship for pivoting the puncturing instrument about the isocenter around the second rotational axis.

A patient lies on a moveable table top, which table top is moves so that a targeted object within the patient's body overlies the isocenter of the fluoro X-ray apparatus as determined by viewing two images. The puncturing instrument always aiming to the targeted object can be pivoted about the isocenter for selecting the most desirable path of penetration without a need for re-aiming same to reach the target.

3 Claims, 3 Drawing Sheets

ORBITAL AIMING DEVICE

BACKGROUND OF THE INVENTION

1. Field of Invention

The present invention relates to a field of medical instrumentation used in conjunction with fluoroscopy in diagnostic penetration of a body to collect a sample and, more specifically, to an orbital aiming device for aiming a puncturing instrument to the isocenter of a fluoroscopic apparatus wherein a targeted object is positioned.

2. Prior Art

The use of puncturing instruments for collecting samples of tissues or fluids in diagnostic examinations is well known. Well known is also the use of fluoroscopic imaging for locating a targeted object within a body and for aiming and guiding the needle. Images are two dimensional, therefore, a minimum of two views are required for three dimensional orientation. It is a trial and error procedure, relatively long, difficult to execute due to the necessity of simultaneously guiding the needle and observing its path on the screen. Fatigue of human hand and the patient movement also can be a source of errors.

To improve upon the procedure, one of the two angular coordinates of spatial orientation was fixed in the prior art to assure the straight-line alignment of the needle to the target, but still the second coordinate, the depth of penetration, was left variable (U.S. Pat. No. 4,750,487).

SUMMARY OF THE INVENTION

An orbital aiming device according to this invention fixes both angular coordinates, thus, assure both the needle alignment and the depth of its penetration.

Another advantage of the present invention is that it allows for real time selecting of the penetration path by pivoting the needle about the targeted object and observing it on the screen without the need of re-alignment.

The orbital aiming device supports the puncturing instrument so that it aims to an isocenter of a fluoro X-ray apparatus isocentric about at least one rotational axis, that is having a point on its radiation axis, the isocenter, which point does not move in space when the radiation axis is rotated about this rotational axis. A targeted object is positioned at the isocenter by placing a patient on a movable table top and moving the top so that a targeted object overlies the isocenter as determined by viewing two images.

The orbital aiming device in order to offer most advantages should be isocentric about two rotational axes which point of intersection defines its isocenter and is disposed in relation to the fluoro X-ray apparatus so that its isocenter coincides with the isocenter of the apparatus. Therefore, the puncturing instrument can be pivoted about these two rotational axes, thus, the isocenter, without changing its alignment.

DETAILED DESCRIPTION OF THE PRESENTLY PREFERRED EMBODIMENT

Figure 3:
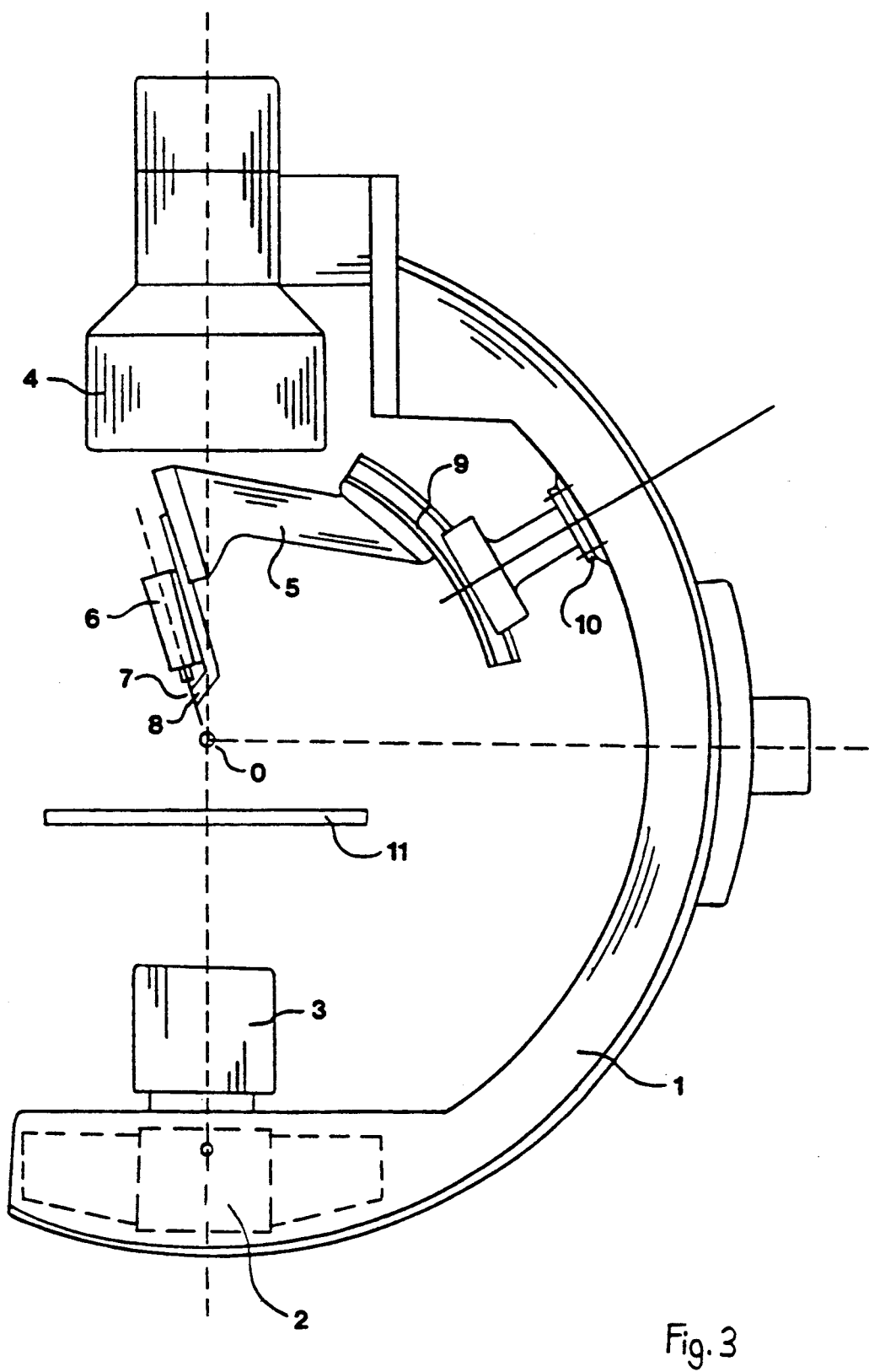
FIG. 3 is an elevation view of the presently preferred embodiment.

Referring to FIG. 3, the orbital aiming device is shown attached to a C-arm 1 carrying an X-ray tube 2 with a collimator 3 having cross-hairs in the center of the beam and an image receptor 4. The C-arm is isocentric about two rotational axes with the isocenter at point 0 on the radiation axis defined by the X-ray tube and the image receptor. The isocenter remains at the same point 0 in space when the radiation axis is rotated about the two rotational axes.

Figure 1:
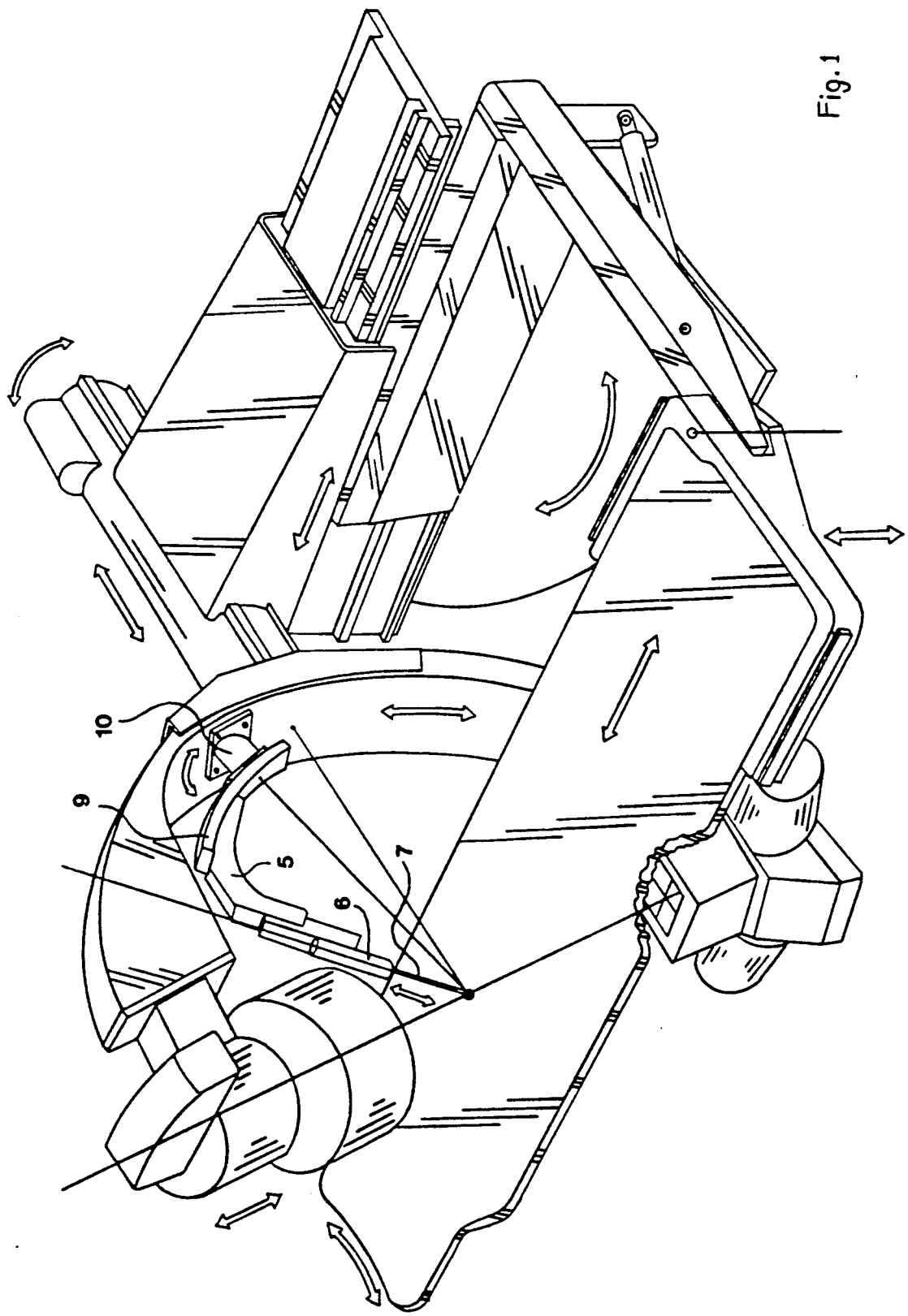
FIG. 1 is a pictorial view of the present invention used with a C-arm fluoroscopic equipment.
Figure 2:
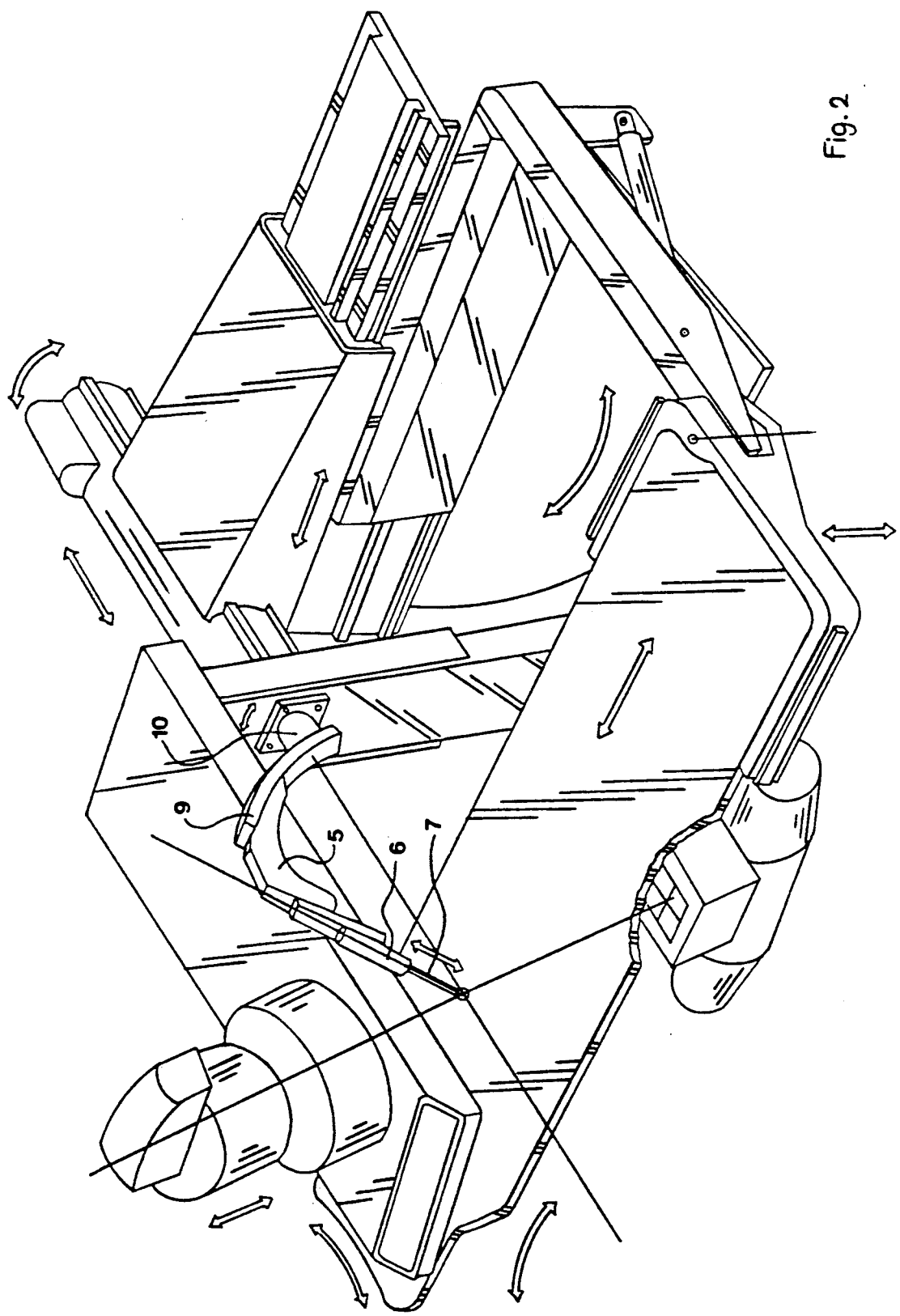
FIG. 2 is a pictorial view of the present invention used with a U-arm fluoroscopic equipment.

The orbital aiming device comprises an elongated member 5 having a puncturing instrument including a biopsy gun 6 with a needle 7 movably mounted thereon so that the needle aims at the isocenter 0; the biopsy gun with the needle is linearly displaceable to a manually adjusted stop 8 which controls the depth of the needle penetration. The elongated member 5 is mounted on an arcuate rail system 9 for a relative orbital movement therebetween and, hence, for pivotal movement of the needle tip about the isocenter 0. The arcuate rail system 9 is shown to include two arcuate components coupled in a telescopic relationship for providing an extended orbital travel of the elongated member 5 without compromising compactness of the device. The arcuate rail system 9 is rotatably attached to a rotational means 10 and rotatable about an axis R for pivotal movement of the needle tip about the isocenter. The rotational means is attached, for example, to the C-arm or U-arm (FIG. 2) by a connecting means providing for prompt attachment and detachment of the device if desirable to gain more access to a patient. The connecting means that the isocenter of the orbital aiming device overlies the isocenter of the fluoroscopic imaging system.

An initial calibration of the orbital aiming device is carried out without a patient by viewing the needle on the fluoroscopic screen to align it to the cross-hair in one view and to adjust the stop 8 in the second view so that the needle points to the cross-hairs.

Then, the patient is positioned on a movable table top 11 and the table top is moved in three directions so that the targeted object overlies the isocenter, that is, overlies the cross-hairs in at least two views. The needle tip is now pivoted for selecting a path of penetration, so that vital organs are avoided and the needle aims between ribs.

We claim:

1. A fluoroscopic imaging system including an orbital aiming device for aiming and guiding a puncturing instrument to an isocenter of a fluoroscopic imaging system and providing a pivoting motion of said puncturing instrument about said isocenter, wherein:

said fluoroscopic imaging system includes a rotationally mounted X-ray support means carrying an X-ray tube and an X-ray image receptor at opposite ends thereof, said X-ray tube and said X-ray image receptor defining a radiation axis, and is isocentric about a rotational axis so that there is a point on said radiation axis, the isocenter, which point does not move in space when the radiation axis is rotated about said one or more rotational axes passing through said isocenter;

said orbital aiming device comprising:

an arcuate rial means coupled to said X-ray support means and adapted for rotational movement with respect to the support means about a rotational axis passing through said isocenter;

an arm means supporting a puncturing instrument so that the puncturing instrument aims at the isocenter, said arm means coupled to said arcuate rail means and adapted for an arcuate motion therealong for providing a pivoting motion of the puncturing instrument about the isocenter.

2. A fluoroscopic imaging system as in claim 1 wherein said arcuate rail means is coupled to said X-ray support means by a connecting means permitting an attachment and detachment of said arcuate rail means and assuring the retention of the alignment of said puncturing instruments on said isocenter.

3. A fluoroscopic imaging system as in claim 1 wherein said arcuate rail means include two arcuate components coupled in sliding engagement with one another for extended orbital travel of said arm means.

* * * * *